United States Patent [19]
Morozov et al.

[11] Patent Number: 5,814,611
[45] Date of Patent: *Sep. 29, 1998

[54] PHARMACEUTICAL FOR THE THERAPY OF IMMUNE DEFICIENCY CONDITIONS

[75] Inventors: Vyacheslav Grigorievich Morozov; Vladimir Khatskelevich Khavinson, both of St. Petersburg, Russian Federation

[73] Assignee: Cytoven J.V., Kirkland, Wash.

[*] Notice: The term of this patent shall not extend beyond the expiration date of Pat. No. 5,538,951.

[21] Appl. No.: 482,121

[22] Filed: Jun. 7, 1995

Related U.S. Application Data

[63] Continuation of Ser. No. 337,341, Nov. 10, 1994, Pat. No. 5,538,951, which is a continuation of Ser. No. 194,189, Feb. 8, 1994, abandoned, which is a continuation of Ser. No. 132,617, Oct. 7, 1993, abandoned, which is a continuation of Ser. No. 6,680, Jan. 21, 1993, abandoned, which is a continuation of Ser. No. 856,802, Mar. 24, 1992, which is a continuation of Ser. No. 415,283, filed as PCT/SU88/00255, Dec. 14, 1988.

[51] Int. Cl.$^6$ ............................. A61K 38/05; C07K 5/072
[52] U.S. Cl. ............................. 514/19; 562/563; 548/496
[58] Field of Search ............................. 514/19; 562/563; 548/496

[56] References Cited

U.S. PATENT DOCUMENTS

| | | | |
|---|---|---|---|
| 4,428,938 | 1/1984 | Kisfaludy et al. | 424/177 |
| 4,473,554 | 9/1984 | Umezawa et al. | 424/177 |
| 4,699,898 | 10/1987 | Gottlieb | 514/18 |
| 4,751,216 | 6/1988 | Gottlieb | 514/18 |
| 5,106,616 | 4/1992 | McAnalley et al. | 424/85.2 |

FOREIGN PATENT DOCUMENTS 0 240 033  10/1987  European Pat. Off. ....... A61K 37/02

OTHER PUBLICATIONS

Declaration of John S. Sundsmo.

N.S. Gee and A.J. Kenny (1987) *Biochem. J.* 246:97–102. Proteins of the kidney microvillar membranes.

G. Belokrylov et al. (1986) *Eksp. Biol. Medit.* 102:51–53. Ability Of Some Amino Acids Incorporated Into Protein To Stimulate The Thymus–Dependent Immune Response.

G. R. Pettit (1975) *Synthetic Peptides,* vol. 3, Academic Press, New York, New York, pp. 130, 134, 143, 424, 427, 429, 434.

H. Sievertsson et al. (1971) *Journal of Medicinal Chemistry,* 15(1):8–11. Synthesis of Di–and Tripeptides and Assay in Vivo for Activity in the Thyrotrol Releasing Hormone and the Luteinizing Releasing Hormone Systems.

Chem. Abstr. 116(17) 171986u (1990).

Chem. Abstr. 111(17) 146389r (1989).

Sandstrom et al. (1987) *Drugs* 34:372–390. Antiviral Therapy in AIDS Clinical Pharmacological Properties and Therapeutic Experience to Date.

Remington's Pharmaceutical Sciences, 1980, pp. 996–997, 1465–1469, 1553–1557.

Jaroff, *Time* May 23, 1988, pp. 56–64. Stop That Germ!.

*ASM News* vol. 56 1990, p. 368.

Basmajian et al. (1982) *Stedman's Medical Dictionary* p. 1139.

*Primary Examiner*—Christine M. Nucker
*Assistant Examiner*—Benet Prickril
*Attorney, Agent, or Firm*—Townsend and Townsend and Crew LLP

[57] ABSTRACT

A pharmaceutical preparation for the therapy of immune deficiency conditions comprising an active principle—a peptide of the structure: H—L—Glu—L—Trp—OH and a pharmaceutically acceptable vehicle.

6 Claims, No Drawings

PHARMACEUTICAL FOR THE THERAPY OF IMMUNE DEFICIENCY CONDITIONS

This application is a continuation of 08/337,341, filed Nov. 10, 1994 which is a continuation of 08/194,189, filed Feb. 8, 1994, abandoned, which is a continuation of 08/132,617, filed Oct. 7, 1993, abandoned, which is a continuation of 08/006,680, filed Jan. 21, 1993, abandoned, which is a continuation of 07/856,802, filed Mar. 24, 1992, abandoned, which is a continuation of 07/415,283, filed Aug. 30, 1989, abandoned, which is a national stage application of PCT/SU88/00255, filed Dec. 14,1988, which has priority to USSR 4352833, filed Dec. 30, 1987.

FIELD OF THE INVENTION

The present invention relates to pharmacology and, in particular, to a novel pharmaceutical preparation for the therapy of immune deficiency conditions.

STATE OF THE ART

Known in the art are preparations for the treatment of immune deficiency conditions, in particular preparations of thymus obtained from animal raw materials: thymosin fraction 5 (cf. Goldstein A.L., Guha A., Zatz M.M., Hardy H.A., White A., Proc. Nat. Acad. Sci., USA, 1972, vol. 69, p. 1800–1803), thymalin (CH, A, 659586), T-activin (US, 4377511). These preparations comprise a complex of substances of a polypeptide nature which are capable of controlling different stages of proliferation and differentiation of T-lymphocytes. However, a practical administration of such preparations is substantially hampered due to complexity of processes for their manufacture, a low yield of active substances, and considerable variation of their physico-chemical and biological properties. Furthermore, due to the presence of ballast components in natural preparation of thymus, in some cases side reactions appear in patients upon use of these preparations.

One of the most effective agents for the treatment of immune deficiency conditions is thymalin comprising a complex of polypeptides with a molecular mass of 600–6,000 Dalton in a pharmaceutically acceptable vehicle such as glycine. It is administered in a dose of up to 10 mg of an active principle once a day for 5 days. The content of active components in this preparation causes its application in high doses (up to 50 mg per the treatment cause).

DISCLOSURE OF THE INVENTION

The present invention is directed to a pharmaceutical preparation for the treatment of immune deficiency conditions incorporating such an active principle of a peptide nature which would ensure a higher biological activity of the preparation, its low toxicity and lack of side effects.

This problem is solved by a pharmaceutical preparation or the therapy of immune deficiency conditions comprising an active principle of a peptide nature and a pharmaceutically acceptable vehicle. The preparation contains, according to the present invention, as the active principle of the peptide nature, a peptide of the following structure:

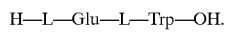

H—L—Glu—L—Trp—OH.

The pharmaceutical preparation according to the present invention for the therapy of immune deficiency conditions has a high activity—in a dose by 50–500 times lesser than that of thymalin it has a pronounced immunostimulant effect in the case of radiation induced immune deficiency. Under the influence of the preparation there is observed a considerable stimulation of the production of lymphocytes and T-lymphocytes, as well as a clearly pronounced modulation of the ratio between subpopulations of immunocompetent cells. The $LD_{50}$ of the preparation according to the present invention could not be established, since upon a 1000- times increase of the therapeutic dose (1 mg/kg), the lethal outcome was not revealed in any of the animals.

The preparation according to the present invention does not cause any side effects.

It is advisable, that the pharmaceutical preparation according to the present invention would contain, when used as an injectable solution, the active principle in an amount of from 0.001 to 0.01 %by weight.

In accordance with the present invention it is also advisable that the pharmaceutical preparation contain, as the pharmaceutically acceptable vehicle, a 0.9% aqueous solution of sodium chloride or a 0.5% solution of novocain.

It is desirable, according to the present invention, that the pharmaceutical preparation in the form of tablets, suppositoria or capsules contain the active principle in the amount of 0.1 mg per tablet, suppositorium or capsule.

It is also desirable, according to the present invention, that the pharmaceutical preparation in the form of tablets, suppositoria or capsules contain the active principle in the amount of 0.1 mg per tablet, suppositorium or capsule.

It is also desirable, according to the present invention, that the pharmaceutical preparation in the form of tablets, suppositoria or capsules would contain, as the pharmaceutically acceptable vehicle, a filler such as starch, glucose, glycine.

Other objects and advantages of the present invention will now become more fully apparent from the following detailed description of the pharmaceutical preparation for the therapy of immune deficiency conditions.

BEST MODE FOR CARRYING OUT THE INVENTION

The pharmaceutical preparation for the therapy of immune deficiency conditions according to the present invention incorporates a peptide of the following structure: H—L—Glu—L—Trp—OH and a pharmaceutically acceptable vehicle.

This peptide can be obtained by a conventional two-stage chemical synthesis in solution on the basis of an activated ether—protected derivative of L-glutamic acid and L-tryptophane. After elimination of the protection groups and a chromatographic purification, the peptide is lyophilized and obtained as an amorphous powder.

The peptide of the structure H—L—Glu—L—Trp—OH comprises a white lyophilized powder readily soluble in water, dimethylformamide, insoluble in chloroform and ether. $[d]^{22}D=+12.6$; C=0.5 $H_2O$. $R_f=0.65$ (butanol:acetic acid:water=3.1:1). The maximum of absorption in the UV-region is 275±5 nm. In the NMR spectrum at 500 MHz, 0.001 mol/l of the peptide solution, there are the following signals from the corresponding aminoacid residues:

Trp—3.17; 3.37; 4.57; 7.16; 7.24; 7.71; 7.49

Glu—1.90; 1.96; 2.21; 3.72.

The above-given data clearly prove the structure of the synthesized compound—the active principle of the pharmaceutical preparation according to the present invention.

The active principle of the pharmaceutical preparation according to the present invention can be used as a free peptide and in the form of water-soluble salts thereof such as sodium, potassium, ammonium, zinc salts.

The preparation according to the present invention can be used in different pharmaceutical forms such as tablets, solutions (injection-intended and intranasal), drops, ointments and suppositoria. It is preferable to use the preparation according to the present invention as injectable solutions with a content of the active principle of from 0.001 to 0.01% by weight (0.0001–0.001 mg/kg of the body-mass, or 10–100 μg of the active principle per 1 ml of the solvent). As the pharmaceutically acceptable vehicle for the injection form, the preparation can incorporate substantially any pharmaceutically acceptable solvent such as an aqueous solution of sodium chloride, distilled water, or a solution of novocain for injections, Ringer's solution, and a solution of glucose.

The preparation according to the present invention in the form of tablets and suppositoria preferably contains the active principle in the amount of 0.1 mg per one tablet or suppositorium. As the pharmaceutically acceptable vehicle for tablets, it is advisable to use starch, glucose, glycine; for suppositoria, it is preferable to use, as the pharmaceutically acceptable vehicle, any suitable pharmaceutic base.

The pharmaceutical preparation according to the present invention shows a high effectiveness in the treatment of immune deficiency conditions, it has a strong influence on the immunological responsiveness of the organism, contributes to a considerable stimulation of the production of lymphocytes or T-lymphocytes and a pronounced modulation of the ratio between subpopulations of immunocompetent cells.

The preparation is not toxic, it is administered in low single and course doses and has a wide spectrum of the therapeutic action. The preparation according to the present invention can be widely employed in medical practice for the therapy and prophylaxis of a whole number of human diseases.

The pharmaceutical preparation according to the present invention for the treatment of immune deficiency conditions has been experimentally studied on animals and in clinics on human beings.

The biological activity of the preparation according to the present invention based on a dipeptide, as compared to the activity of thymalin, was studied in the cases of secondary immune deficiency conditions, in particular those induced by radiation. The study was carried out on male guinea pigs with a mass of 159–200 g. The animals were irradiated in a special unit with the dose of 1 Gr. One day after the irradiation, the test groups of animals (10 guinea pigs in each group) were administered with thymalin and with the preparation according to the present invention in the doses of 0.0001–0.001 mg/kg in 0.5 ml of a 0.9% aqueous solution of sodium chloride intramuscularly every day during 3 days. The control group of animals was administered with 0.5 ml of a 0.9% aqueous solution of sodium chloride following the same scheme. On the 10th day after the irradiation in thymus and in the spleen, the number of karyocytes, T- and B-lymphocytes was determined by the method of rosette formation.

The obtained results are shown in Tables 1 and 2 hereinbelow. It has been found that the dipeptide in the dose of 0.001 mg/kg provides an immunostimulant effective by increasing, by more than 3 times, the number of karyocytes and T-lymphocytes in the thymus of the irradiated animals. In addition, the dipeptide in the dose of 0.001 mg/kg normalizes the content of B-lymphocytes in the thymus and the spleen of the irradiated animals. Thymalin in all the studied doses does not exert a certain influence on the cell composition of the thymus and spleen of the irradiated animals.

TABLE 1

Comparative Study of the Effect of the Preparation According to the Present Invention and of Thymalin on the Cell Composition of Irradiated Guinea Pigs (X ± m)

| Group of Animals | Number of Karyocytes, (thous./mg) | Number of T-lymphocytes (thous./mg) | Number of B-lymphocytes (thous./mg) |
|---|---|---|---|
| Intact | 481.4 ± 21.3 | 378.5 ± 25.5 | 4.8 ± 0.3 |
| Control (irradiation) | 87.4 ± 13.2 | 49.6 ± 5.6 | 5.7 ± 0.6 |
| Dipeptide (0.00001 mg/kg) | 89.3 ± 10.7 | 51.3 ± 6.7 | 5.3 ± 0.5 |
| Dipeptide (0.00001 mg/kg) | 139.8 ± 14.1$^x$ | 89.4 ± 9.1$^x$ | 4.9 ± 0.5$^x$ |
| Dipeptide (0.001 mg/kg) | 275.8 ± 26.4$^x$ | 194.7 ± 21.3$^x$ | 3.3 ± 0.4$^x$ |
| Thymalin (0.00001 mg/kg) | 85.4 ± 11.6 | 53.6 ± 7.2 | 5.4 ± 0.6 |
| Thymalin (0.0001 mg/kg) | 90.4 ± 9.7 | 46.3 ± 5.7 | 5.3 ± 0.5 |
| Thymalin (0.001 mg/kg) | 89.1 ± 13.6 | 47.9 ± 6.1 | 5.7 ± 0.7 |

$^x$statistically confident (P < 0.05) as compared to the control.

TABLE 2

Comparative Study of the Effect of the Preparation According to the Present Invention and of Thymalin on the Cell Composition of the Spleen of Irradiated Guinea Pigs (X ± m)

| Group of Animals | Number of Karyocytes, (thous./mg) | Number of T-lymphocytes (thous./mg) | Number of B-lymphocytes (thous./mg) |
|---|---|---|---|
| Intact | 409.3 ± 25.6 | 40.4 ± 2.9 | 72.5 ± 5.4 |
| Control (Irradiation) | 147.9 ± 23.2 | 29.8 ± 3.4 | 51.4 ± 4.3 |
| Preparation of the Invention (0.00001 mg/kg) | 150.6 ± 15.8 | 31.2 ± 3.6 | 50.9 ± 5.4 |
| Preparation of the Invention (0.0001 mg/kg) | 148.3 ± 16.0 | 30.4 ± 3.9 | 62.4 ± 6.1$^x$ |
| Preparation of the Invention (0.001 mg/kg) | 146.6 ± 18.1 | 29.9 ± 3.3 | 73.2 ± 5.1$^x$ |
| Thymalin (0.00001 mg/kg) | 151.4 ± 16.7 | 32.0 ± 4.1 | 53.7 ± 6.3 |
| Thymalin (0.0001 mg/kg) | 147.3 ± 15.1 | 31.7 ± 5.2 | 49.7 ± 5.8 |
| Thymalin (0.001 mg/kg) | 150.0 ± 16.6 | 28.9 ± 4.1 | 54.7 ± 5.2 |

$^x$Statistically confident (P < 0.05) as compared to the control.

From the results obtained in an additional series of experiments under similar conditions, it has been found that thymalin provides an immunostimulating effect only in the dose of 0.1 mg/kg of the animal's body mass (see the data of Table 3 hereinbelow).

TABLE 3

Effect of Thymalin on Cell Composition of the Thymus and Spleen of Irradiated Guinea Pigs (X ± m)

| Group of Animals | Number of Karyocytes (thous./mg) | |
|---|---|---|
| 1 | Thymus 2 | Spleen 3 |
| Intact | 481.4 ± 21.3 | 409.3 ± 25.6 |
| Control (irradiation) | 87.4 ± 13.2 | 147.9 ± 23.2 |
| Thymalin | 89.3 ± 11.6 | 153.6 ± 17.1 |

TABLE 3-continued

Effect of Thymalin on Cell Composition of the Thymus and Spleen of Irradiated Guinea Pigs (X ± m)

| | | |
|---|---|---|
| Thymalin (0.01 mg/kg) | | |
| Thymalin (0.05 mg/kg) | 101.4 ± 15.3 | 149.4 ± 16.0 |
| Thymalin (0.1 mg/kg) | 280.7 ± 27.3[x] | 154.3 ± 16.1 |

| Group of Animals | Number of Karyocytes (thous./mg) | | Number of Karyocytes (thous./mg) | |
|---|---|---|---|---|
| 1 | Thymus 4 | Spleen 5 | Thymus 6 | Spleen 7 |
| Intact | 378.5 ± 25.5 | 40.4 ± 2.9 | 4.8 ± 0.3 | 72.5 ± 5.4 |
| Control (irradiation) | 49.6 ± 5.6 | 29.8 ± 3.4 | 5.7 ± 0.6 | 51.4 ± 4.3 |
| Thymal in (0.01 mg/kg) | 51.3 ± 7.8 | 33.6 ± 5.7 | 5.9 ± 0.7 | 54.5 ± 6.3 |
| Thymal in (0.05 mg/kg) | 73.7 ± 14.1 | 26.4 ± 4.1 | 5.1 ± 0.6 | 61.7 ± 9.0 |
| Thymal in (0.1 mg/kg) | 206.7 ± 19.8[x] | 30.1 ± 3.3 | 3.9 ± 0.5[x] | 75.6 ± 6.2[x] |

[x]Statistically confident as compared to the control ($P < 0.05$).

Therefore, the preparation according to the present invention in a dose by 50–500 times smaller than thymalin exhibits a clearly pronounced immunostimulant effect in the case of radiation induced immune deficiency.

A comparative assessment of the effect produced by the preparation according to the present invention and that of thymalin on expression of receptors of thymocytes obtained from intact guinea pigs was made. It is known that after treatment of lymphocytes with trypsin there occurs the decomposition of the major portion of E-receptors on the surface of cells, wherefore the percentage of T-lymphocytes is reduced which is revealed in the reaction of rosette-formation (E-RFC). The addition of thymus preparations to the trypsin-treated lymphocytes in the restoration of destroyed E-receptors which is revealed in an increased percentage of E-RFC (T-lymphocytes).

The preparation according to the present invention and thymalin were added to thymocytes obtained from 10 intact guinea pigs in a dose ranging from 0.0001–1 μg/ml. The results of the study are shown in Table 4 hereinbelow.

It has been found that the preparation according to the present invention and thymalin restored E-receptors of thymocytes treated with trypsin. The preparation according to the present invention was effective in a dose of from 0.01 to 1 μg/ml.

The assessment of clinico-immunological effectiveness of the pharmaceutical preparation according to the present invention was made on 300 patients with purulent-inflammatory diseases of bones and soft tissues (chronic post-traumatic osteomyelitis of long tubular bones, purulent-inflammatory complications of trauma and operative interventions in the case of diseases of the locomotor system, acute and chronic purulent-inflammatory diseases of bones and soft tissues of maxillofacial area, staphylococcal pyoderma).

TABLE 4

Effect of the Preparation According to the Present Invention on Expression of E-receptors of Thymocytes (X ± m)

| Preparation | EA - RFC (%) | P |
|---|---|---|
| Control | 36.1 ± 3.1 | — |
| Preparation of the Present Invention (0.0001 μg/ml) | 37.4 ± 4.0 | >0.05 |
| Preparation of the Present Invention (0.001 μg/ml) | 41.4 ± 5.1 | >0.05 |
| Preparation of the Present Invention (0.01 μg/ml) | 61.4 ± 5.3 | <0.05 |
| Preparation of the Present Invention (1 μg/ml) | 62.7 ± 6.1 | <0.05 |
| Thymalin (0.0001 μg/ml) | 35.3 ± 3.9 | >0.05 |
| Thymalin (0.001 μg/ml) | 39.6 ± 4.1 | >0.05 |
| Thymalin (0.01 μg/ml) | 38.7 ± 4.0 | >0.05 |
| Thymalin (1 μg/ml) | 57.0 ± 4.7 | <0.05 |

The pharmaceutical preparation according to the present invention was intramuscularly or intranasally administered in a single dose of 100 μpg for 3–10 days (500 μg of the preparation on the average per course). The control group was composed of 200 patients with a similar pathology.

In the patients with purulent-inflammatory diseases of bones and soft tissues of different localization, there has been revealed, to a different extent, of quantitative and especially functional characteristics of the cell immunity and of non-specific resistance. Also noted is the violation of differentiation of subpopulations of T-cells: a reduced number of T-helpers (OKT4$^+$) and T-suppressors (OKT8$^+$).

The use of the pharmaceutical preparation according to the present invention contributed to an improvement of the clinical progress of the disease or to healing in 75.3–91.7% of patients which was revealed in a reduced period of cleansing and healing of wounds, diminution of the area of destruction of the bone tissue, in a faster arresting of purulent-inflammatory diseases of the skin, shortening of the treatment time by 20–30% as compared to the control patients. The clinical effectiveness of the preparation according to the present invention was accompanied by restoration of both quantitative and functional characteristics of the T-system of immunity and non-specific resistance.

In none of the cases of clinical applications of the preparation according to the present invention toxic or allergic reactions were noticed.

A comparative assessment of the effect of the preparation according to the present invention and of thymalin was made on subpopulation of lymphocytes in patients with different pathologies, namely: for T-helpers (OKT4$^+$), T-suppressors (OKT8$^+$), coefficient of differentiation OKT4$^+$/OKT8$^+$ and B-lymphocytes (Ig$^+$) in patients with thymomegalia, thymectomy, rheumatoid arthritis, furunculosis and breast cancer (after radiation therapy). In cultures of lymphocytes of the peripheral blood of the patients, the percentage of subpopulations of lymphocytes was determined by the immunofluorescent method using monoclonal antibodies prior to and after introduction of thymalin and the preparation of the present invention in the most effective doses of 1 μg/ml and 0.01 μg/ml respectively.

The results of the studies are shown in Tables 5 and 6.

TABLE 5

Effect of Thymalin on Subpopulations of Lymphocytes in Patients with Different Pathologies (in the Numerator - the Starting Amount, in the Denominator - After the Addition of Thymalin)

| Pathology | Number of Experiments | t-Helpers (OKT4+) | T-Suppressors (OKT8+) | OKTA+ / OKT8+ | B-Lymphocytes (Ig+) |
|---|---|---|---|---|---|
| Healthy | 10 | 35.3 ± 2.7 / 38.2 ± 2.9 | 21.3 ± 0.9 / 18.8 ± 0.8 | 1.66 ± 0.13 / 2.03 ± 0.16$^x$ | 13.8 ± 1.2 / 12.1 ± 1.1 |
| Thymomegalia | 8 | 23.4 ± 1.7 / 32.6 ± 2.8$^x$ | 8.2 ± 1.0 / 19.7 ± 1.7$^x$ | 2.85 ± 0.19 / 1.65 ± 0.11$^x$ | 16.4 ± 1.3 / 11.4 ± 1.1 |
| Thymectomy | 4 | 10.5 ± 1.3 / 20.6 ± 1.7$^x$ | 14.5 ± 0.7 / 16.1 ± 1.1 | 0.72 ± 0.08 / 1.28 ± 0.11$^x$ | 12.5 ± 1.0 / 17.7 ± 1.3$^x$ |
| Rheumatoid Arthritis | 4 | 20.8 ± 1.4 / 29.5 ± 1.7$^x$ | 26.5 ± 2.1 / 22.3 ± 1.7 | 0.78 ± 0.09 / 1.32 ± 0.11$^x$ | 8.9 ± 0.9 / 14.3 ± 1.2 |
| Furunculosis | 6 | 16.6 ± 1.2 / 26.9 ± 1.1$^x$ | 12.0 ± 0.9 / 18.3 ± 1.3$^x$ | 1.30 ± 0.82 / 1.47 ± 1.2$^x$ | 19.9 ± 1.7 / 15.6 ± 1.2 |
| Breast Cancer (After Radiation Therapy) | 10 | 23.3 ± 2.1 / 32.6 ± 3.4$^x$ | 21.3 ± 1.7 / 19.8 ± 1.6 | 1.09 ± 0.04 / 1.65 ± 0.09$^x$ | 15.6 ± 1.2 / 13.6 ± 1.0 |

$^x$Statistically confident (P < 0.05) as compared to the initial characteristics.

TABLE 6

Effect of the Preparation According to the Present Invention on Subpopulations of Lymphocytes in Patients with Different Pathologies

| Pathology | Number of Experiments | T-Helpers (OKT4+) | T-Suppressors (OKT8+) | OKT4+ / OKT8+ | B-Lymphocytes (Ig+) |
|---|---|---|---|---|---|
| Healthy | 18 | 35.4 ± 2.7 / 37.6 ± 2.3 | 21.2 0.9 / 19.4 0.9 | 1.66 ± 0.13 / 1.94 ± 0.11 | 13.8 ± 1.2 / 12.6 ± 1.3 |
| Thymomegalia | 8 | 23.4 ± 1.7 / 33.4 ± 2.6$^x$ | 8.2 ± 1.0 / 18.3 ± 1.6$^x$ | 2.85 ± 0.19 / 1.83 ± 0.12$^x$ | 16.4 ± 1.3 / 12.6 ± 1.3$^x$ |
| Thymectomy | 4 | 10.5 ± 1.3 / 21.1 ± 1.5$^x$ | 14.6 ± 0.7 / 15.3 ± 1.3 | 0.72 ± 0.08 / 1.38 ± 0.09$^x$ | 12.5 ± 1.0 / 16.4 ± 1.2$^x$ |
| Rheumatoid Arthritis | 4 | 20.8 ± 1.4 / 30.1 ± 1.9$^x$ | 26.5 ± 2.1 / 24.7 ± 2.0 | 0.78 ± 0.09 / 1.22 ± 0.12$^x$ | 8.9 ± 0.9 / 14.1 ± 1.3 |
| Furunculosis | 6 | 16.6 ± 1.2 / 27.4 ± 1.2$^x$ | 12.0 ± 0.9 / 19.1 ± 1.4$^x$ | 1.38 ± 0.82 / 1.43 ± 1.3$^x$ | 19.9 ± 1.7 / 16.4 ± 1.7 |
| Breast Cancer (After Radiation Therapy) | 10 | 23.3 ± 2.1 / 31.7 ± 2.9$^x$ | 21.3 ± 1.7 / 18.6 ± 1.9 | 1.09 ± 0.04 / 1.70 ± 1.5$^x$ | 15.5 ± 1.2 / 14.7 ± 1.2 |

$^x$statistically confident (P < 0.05) as compared to the starting characteristic.

It has been shown that thymalin and the preparation according to the present invention (in a dose nearly 100 times as low as that of thymalin) normalizes the ratio between subpopulations of lymphocytes in all groups of the examined patients.

Therefore, the results of the experimental study of the novel pharmaceutical preparation have shown its high efficiency in the treatment of immune deficiency conditions. As compared to thymalin, the preparation of this invention has a stronger (by about 50–500 times) effect on the immunological reactivity of the organism. The preparation gives rise to a considerable stimulation of the production of lymphocytes and T-lymphocytes, as well as to a clearly pronounced modulation of the ratio between subpopulations of immunocompetent cells.

The preparation according to the present invention can be used in various pharmaceutical forms such as injectable solutions, tablets, suppositoria, ointments. In the case of using the preparation according to the present invention as injectable solutions, the latter contain the active principle in an amount of from 0.001 to 0.01% by weight (0.0001–0.001 mg/kg of the body mass or 10–100 µg of the active principle in 1 ml of the solvent). As the diluent the preparation according to the present invention preferably incorporates a 0.9% aqueous solution of sodium chloride, distilled water, a solution of novocain for injections, Ringer's solution, a solution of glucose.

The pharmaceutical preparation according to the present invention in the form of tablets and suppositoria preferably contains the active principle in the amount of 0.1 mg per tablet or suppositorium. For tablets and suppositoria as a pharmaceutical filler, use is made of any pharmaceutically acceptable vehicle. The preparation in the form of an injectable solution is administered intramuscularly at the rate of one injection during 5 days. The intranasal administration of the preparation is also effected during 5 days at the rate of one ampule or syringe-tube.

The preparation according to the present invention does not have any side effect and has no contraindications against its application. The pharmaceutical forms of the preparation according to the present invention are prepared by conventional methods.

INDUSTRIAL APPLICABILITY

The preparation according to the present invention is useful in the medical practice for the treatment and prevention of immune deficiency conditions of the human organism.

We claim:

1. A method for increasing the number of T-lymphocytes, B-lymphocytes or karyocytes in a subject suffering from staphylococcal pyoderma comprising administering to the subject a pharmaceutical preparation comprising a pharmaceutically acceptable vehicle and a purified dipeptide having the amino acid sequence L—Glu—L—Trp, or a salt of said dipeptide, in an amount sufficient to cause said increase.

2. The method of claim 1 wherein the amount is about 0.1 $\mu$g/kg to about 1 $\mu$g/kg body mass of the subject.

3. The method of claim 1 wherein the amount is about 0.2 $\mu$g/kg to 2 $\mu$g/kg body mass of the subject.

4. The method of claim 1 wherein the amount is about 1 $\mu$g/kg body mass of the subject.

5. The method of claim 1 wherein the pharmaceutical composition is administered intramuscularly or intranasally.

6. The method of claim 1 wherein the amount of dipeptide or salt thereof is about 500 $\mu$g administered in several doses.

* * * * *

UNITED STATES PATENT AND TRADEMARK OFFICE
CERTIFICATE OF CORRECTION

PATENT NO. : 5,814,611
DATED : September 29, 1998
INVENTOR(S) : Morozov et al.

It is certified that error appears in the above-identified patent and that said Letters Patent is hereby corrected as shown below:

Title page, item [54] and Col. 1, the title should read

PHARMACEUTICAL <u>PREPARATION</u> FOR THE THERAPY OF IMMUNE DEFICIENCY CONDITIONS

Signed and Sealed this

Second Day of February, 1999

Attest:

Attesting Officer

*Acting Commissioner of Patents and Trademarks*